(12) United States Patent
Peralta

(10) Patent No.: US 6,358,048 B1
(45) Date of Patent: Mar. 19, 2002

(54) PINCH VALVE ASSEMBLY

(76) Inventor: Michael A. Peralta, 4449 CR 207, Liberty Hill, TX (US) 78642

( * ) Notice: Subject to any disclaimer, the term of this patent is extended or adjusted under 35 U.S.C. 154(b) by 0 days.

(21) Appl. No.: 09/568,712

(22) Filed: Jun. 5, 2000

Related U.S. Application Data

(60) Provisional application No. 60/133,658, filed on May 11, 1999.

(51) Int. Cl.$^7$ ............................................. A61C 19/02
(52) U.S. Cl. ....................................................... 433/28
(58) Field of Search ................................... 433/28, 100

(56) References Cited

U.S. PATENT DOCUMENTS

| | | | | |
|---|---|---|---|---|
| 3,672,059 A | * | 6/1972 | Booth | 433/28 |
| 3,755,899 A | * | 9/1973 | Betush | 433/28 |
| 3,986,262 A | * | 10/1976 | Casillas | 433/28 |
| 4,069,587 A | * | 1/1978 | Peralta | 433/28 |
| 4,375,963 A | * | 3/1983 | Betush | 433/28 |
| 4,459,106 A | * | 7/1984 | Peralta et al. | 433/28 |
| 4,806,099 A | * | 2/1989 | Peralta | 433/28 |

* cited by examiner

*Primary Examiner*—Nicholas D. Lucchesi

(57) ABSTRACT

A pneumatic 'Pinch Valve' control assembly for regulating stopping and/or starting the supply of gasses, air and/or water to a tool, or any type of Dental or Laboratory handpiece in response to it's shaft entering and encircling the inner circumference inside a hanger or holder in which it is removably stored.

The assembly comprises of a standard handpiece holder FIG. No. 1a normally referred to as a Universal holder, front section modified for this application and attached to a Back Plate or adapter through which channels are bored to allow flexible air tubing vinyl or other material passage in a horizontal or vertical manner.

A second channel, or well-type recess converges on this 'through channel' which can be either horizontal or vertical to allow for the forward and backward movement of a solid Plunger or an elongated, oval-shaped Disc or a Pressure Lever to 'pinch flat' the walls of the flexible tubing passing through or across the path of the main channel thus restricting the flow of any gasses, air or water. This Plunger, or Disc, or Pressure Lever whichever design may be employed movement is activated when the tool or handpiece or hose coupling pushes either one of these three items back and 'pinches flat' the tube located in the main, cross channel, thus preventing the passage of any gasses, air and/or water. When the tool or handpiece is removed and the Foot Control or any form of control is activated to the ON state to commence the flow of the gasses, air and/or water, the flow pressure forces outward the walls of the flexible tubing and the Plunger, or Disc or Pressure Lever, whichever is applicable, moves forward allowing the tool or handpiece to commence working by delivering the required flow need for optimum turbine performance.

5 Claims, 7 Drawing Sheets

Item 10

FIG> 2b

Item 17

Item 18

Item 16

Item 16

Item 16

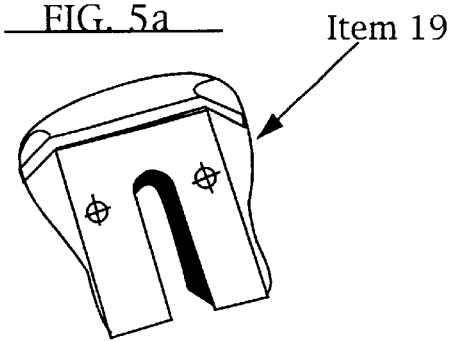
FIG. 5a — Item 19
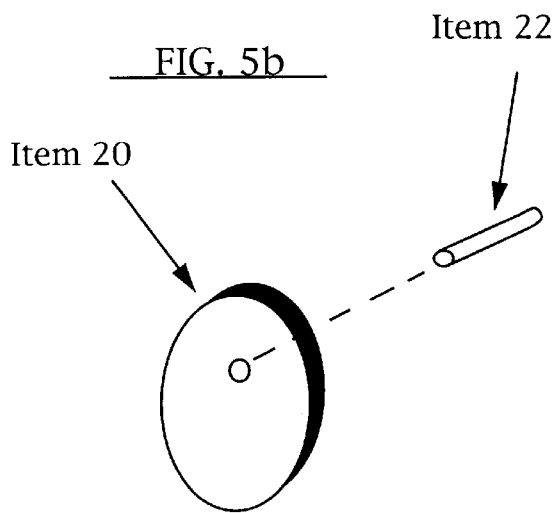
FIG. 5b — Item 20, Item 22
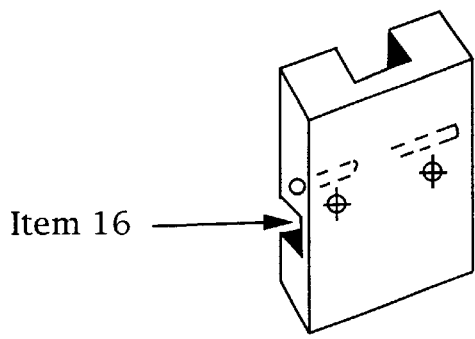
FIG. 5c — Item 16

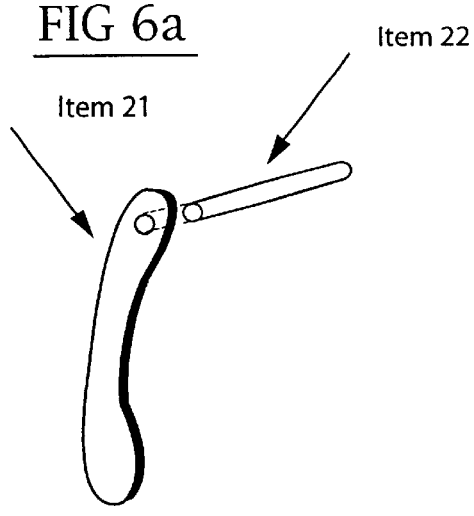
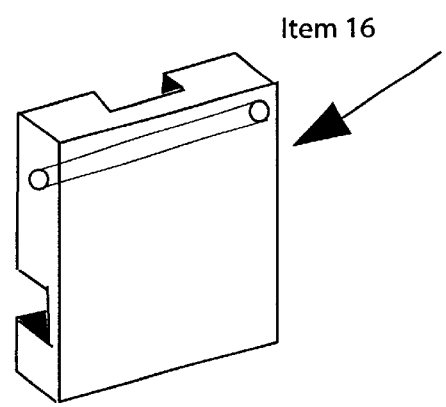

PINCH VALVE ASSEMBLY

This appln claims benefit of Prov. No. 60/133,658 filed May 11, 1999.

BACKGROUND OF THE INVENTION

1. Field of the Invention

This invention relates to a 'Pinch Valve' assembly whose design has not before been presented in this format WITHIN A HANDPIECE HOLDER ASSEMBLY for controlling the delivery of any gas, air and/or water to Medical, Dental, laboratory or other types of delivery systems, but may be used in other Industries where this application could apply.

2. Description of the Prior Art

Conventional Medical, Dental and Laboratory drills are operated at relatively high speeds by an Air Turbine driven from a source of pneumatic air flow at a regulated pressure. These pressures and corresponding flows are controlled by centrally located ON/OFF pre-machined Control Blocks, with internal valving which forms the main functions of the systems. Worldwide these systems use one of the following technologies.

Technology (1) totally pneumatic:

This involves the used of Plungers, Springs, Diaphragms, and various forms of 'O'Rings and other associated interface moving part components preassembled inside. Control Blocks carefully machined internally to close tolerances working in conjunction with secondary air circuits through independent multiple handpiece holder switches, again using the same basic design in miniature form having a plunger with 'O'Rings and a tension spring inserted at the back of each holder; when the tool or handpiece is pushed into the holder, the Instrument hose coupling would actuate the valve by pressing against the plunger thereby creating the OFF state. Withdrawal of the tool or handpiece opens the valve sending an air pressure signal to the Control Block. This signal pressure forces down the internal diaphragm and piston to an open or ON state allowing air flow to commence actuation of the tool or handpiece.

Technology (2) Electro-pneumatic:

These systems involve the use of Electro-pneumatic Solenoid Valves and/or Logic Valves, working in sequence with low voltage signals from micro-switches located at the rear of the handpiece holders. As the tools or handpieces are removed and replace into the holders by the operator, the micro-switches are 'tripped' to actuate the Solenoid Valves in an ON and OFF function of the Air and/or Water flow to the tool or handpiece.

Technology (3) Fluidic Controlled Blocks:

A control arrangement developed by applicant uses a modular pre-machined Fluidic Block design, described in U.S. Pat. No. 4,069,587 dated Jan. 24, 1978 accomplished multiple handpiece switching functions.

Although this Block, with its handpiece holder positions built into it formed a compact way to distribute several airflow circuits, it is operationally dependent upon the accuracy in alignment of a laminar flow of air bridging an air gap across the internal walls of the holder. When the tool or handpiece is removed from the holder, the Laminar air flows across the gap, enters the adjacent aperature and signals the Fluidic device to the ON state.

This design required precise machining operations and expensive to manufacture.

A further improvement to this design for simplicity was carried out in February, 1989 in the form of a Cassette for controlling the supply of air and/or water to a Dental or Laboratory tool or handpiece, as described under U.S. Pat. No. 4,806,099. While simplicity in function was achieved the fabrication of an expensive mold, with inner chambers and involving the use of a Diaphragm, a Plunger and 'O'Rings, made the assembly time consuming with detailed 'Quality Control' checks which did little to reduce production costs. To simplify the ON/OFF function of this Cassette design, original pneumatic handpiece holder switches as used in totally pneumatic systems: Technology (1) are employed for the selection of the tools or handpieces.

Technical Clarification to Technologies (1) and (2):

In both of these two systems a secondary Air or Electronic circuit is need to activate the ON/OFF Control Blocks or Solenoid Valves when the tool or handpiece is removed from its holder.

Commencement of a 'Break-Through' in Simplification

The Medical, Dental and Laboratory industries began recognizing the fact that simpler Delivery systems circuitry were essential to progress, and that pneumatics held the key began employing the 'Pinch Valve' principle.

The two Dental Equipment Manufacturers who spearheaded this move some 17 years ago to try and simplify designs by using the 'Pinch Valve' technique were Proma of California and Ritter of Germany. This was achieved in two forms:

1) Passing flexible vinyl tubing through a Control Block where it is 'pinched flat' by an internal, spring loaded Piston whose ON/OFF action is dependent on the flow of pressurized air being discharged from the Foot Control AND the tool or handpiece being removed from a holder, as described in Technology (1a).

No Basic Change

Although the machining of the Control Block was simplified, the Circuit itself still required a secondary Air Circuit in order to function.

2) The Proma Company struggled to break away from this form of basic circuitry by introducing a form of 'Pinch Valve' technique whereby the flexible vinyl tubing was passed between solid, round rollers connected to outstretched, metal arms. At the end of the arms, one for each tool or handpiece were positioned the handpiece holders. When the tool or handpiece is removed from the holder AND the operator, physically pushes UPWARD on the arm, this releases the tension or 'pinching action' on the tube being pinched flat by the roller and the Drive Air commences to flow, when the Foot Control is depressed by the operator.

At this Point: (as the date of this Patent Application)

No known further advancements have been manufactured and sold, to change and/or improve on these types of 'pinching' devices.

A substantial need has developed for a far more simplified Control Delivery system, which totally eliminates the use of the following:

1) Pneumatic Control Blocks whose function depends on the internal actuation of Diaphragms, Plungers, and Springs.

2) Logic Valves using precisely machined or molder interface moving parts.

3) Distribution Manifolds with their maze of tubing circuitry.

4) Manually operated selector components commonly termed 'Routing Valves'.

5) Solenoid Valves with their electronic circuit boards and associated components.

While concentrating on the elimination of these components to also build into place a truly simplified circuitry requiring NO EXTENSIVE 'time consuming' Quality Control work while being assembled at the factory or 'ON SITE'.

This control delivery system is designed to arrive at the end user preassembled, ready, ready to be used and requires no special training to 'link up' the two standard air and water supply couplings.

Note

Fluidic: A term used as the science of using very low pressures below 0.007 p.s.i. in accomplishing control functions of excessively high air pressures, Water, Hydraulics or in combination with Electronics, not easily obtainable by other mediums.

SUMMARY OF THE INVENTION

It is the principal object of the Patent Application presented to further clarify and consolidate the previous documentation dated May 11, 1999, Ser. No. 60/133,658, and to describe more fully this distinct 'Pinch Valve' embodiment along with its simplified associated circuitry, specially designed for its function, ease of manufacture and trouble free daily use.

These and other objects are attained in accordance with this designed method of a 'Pinch Valve' system not before presented into the Medical, Dental and Laboratory industries, although may also apply to other industries where this application applies.

It is the further principal object of the present invention to describe the specific manner or method by which the flexible Drive Air tube (vinyl or other material) is 'pressed/pinched flat' INSIDE THE ACTUAL HANDPIECE HOLDER ASSEMBLY itself, thereby totally eliminating the passage of tubing through a Control Block, prior to the handpiece holder, and as a result dispenses with the need for any form of Control Block or associated tubing Distribution Manifold. This design forming the nucleus of this 'Pinch Valve' embodiment.

Furthermore, in conjunction with this handpiece holder 'Pinch Valve' design is incorporated a complete design change in Circuitry (not before presented in the Medical, Dental or Laboratory industries in Control Delivery pneumatic systems). In all previous Control Delivery Equipment Circuitry using pneumatics, used by Manufacturers worldwide, the source of Air Supply goes direct to a Main Air Regulator (which is pre-set) from there the air flows to the variable Foot Control, BEFORE it is distributed via a Distribution Manifold to different circuit components.

The Circuit 'Layout' in an Air flow path in this embodiment of the 'Pinch Valve' design is a distinct change or departure from all other known Delivery Systems, manufactured and sold worldwide. For this reason, the Circuit Layout as shown in FIG. 1 should be considered an integral part of the 'Pinch Valve'. FIG. 1, Item 10, function and consequently part of the Patent Application. NO OTHER CONTROL OR SECONDARY CIRCUIT, either Pneumatic, Electro-pneumatic, Fluidic or Manual selection is necessary for the operation of this 'Pinch Valve' WITHIN A HANDPIECE HOLDER ASSEMBLY as described in this Patent Application as covered under Patent pending Ser. No. 60/133,658 dated May 11, 1999.

It is an even further object of the present invention to 'pin-point' the Patentable assets as applied to this circuit shown in FIG. 1 comprising the ON/OFF feature of the 'Pinch Valve', FIG. 1, Item 10, as an integral part of the Circuitry, and as further described in FIGS: 2, 2a, 2b, 3, 4, 4a and 4b collectively introduced as:

This shows a circuit drawing of the complete system incorporating the 'Pinch Valve' Assembly as shown in Item 10 of the present invention, also the circuitry in Air flow path depicting the Air flow travels from the primary source direct to the Foot Control, then through a Filter to the main Air Regulator for the handpiece controls. These two aspects: First, the 'Pinch Valve' embodiment itself. Second, the directional alignment or order of the Air flow path passing through the Foot Control then to the UNIT MAIN REGULATOR, being a distinct change from systems now being manufactured and sold.

FIGS: 2, 2a, 2b

Showing Bottom View of the holder with front and back views respectively, after the modification machining has been carried out.

FIG. 3

This represents a Cross-sectional view of the round, Plunger Button with 'O'Ring Groove. Rounded end makes contact with handpiece or hose coupling. Flat end creates the 'Pinching action' on the flexible air tube, inside the holder assembly.

FIG. 4

Back Plate used to support or carry the Drive Air tube and provides the strength for the pinching action of the plunger.

FIG. 5

This describes a further embodiment using an elongated oval shaped Disc instead of a Plunger Button to create the 'Pinching' action.

FIG. 5a

Describes a slot (machined in the plastic holder) instead of a hole for the oval shaped Disc to move 'back-and-forward' to create the 'Pinching' action.

FIG. 5b

Describes the Disc with the Fulcrum Pin.

FIG. 5c

This illustrates the Back Plate design FIG. 5c with a slot allowing the Disc FIG. 5b to line up with the holder FIG. 5a as a completed assembly.

FIG. 6

This describes an even further embodiment using a Pressure Lever, FIG. 6a, instead of a Plunger, FIG. No. 3, or an oval shaped flat Disc, FIG. 5b. The handpiece Holder still maintaining the slot design as shown per FIG. 5a.

Figure 1:
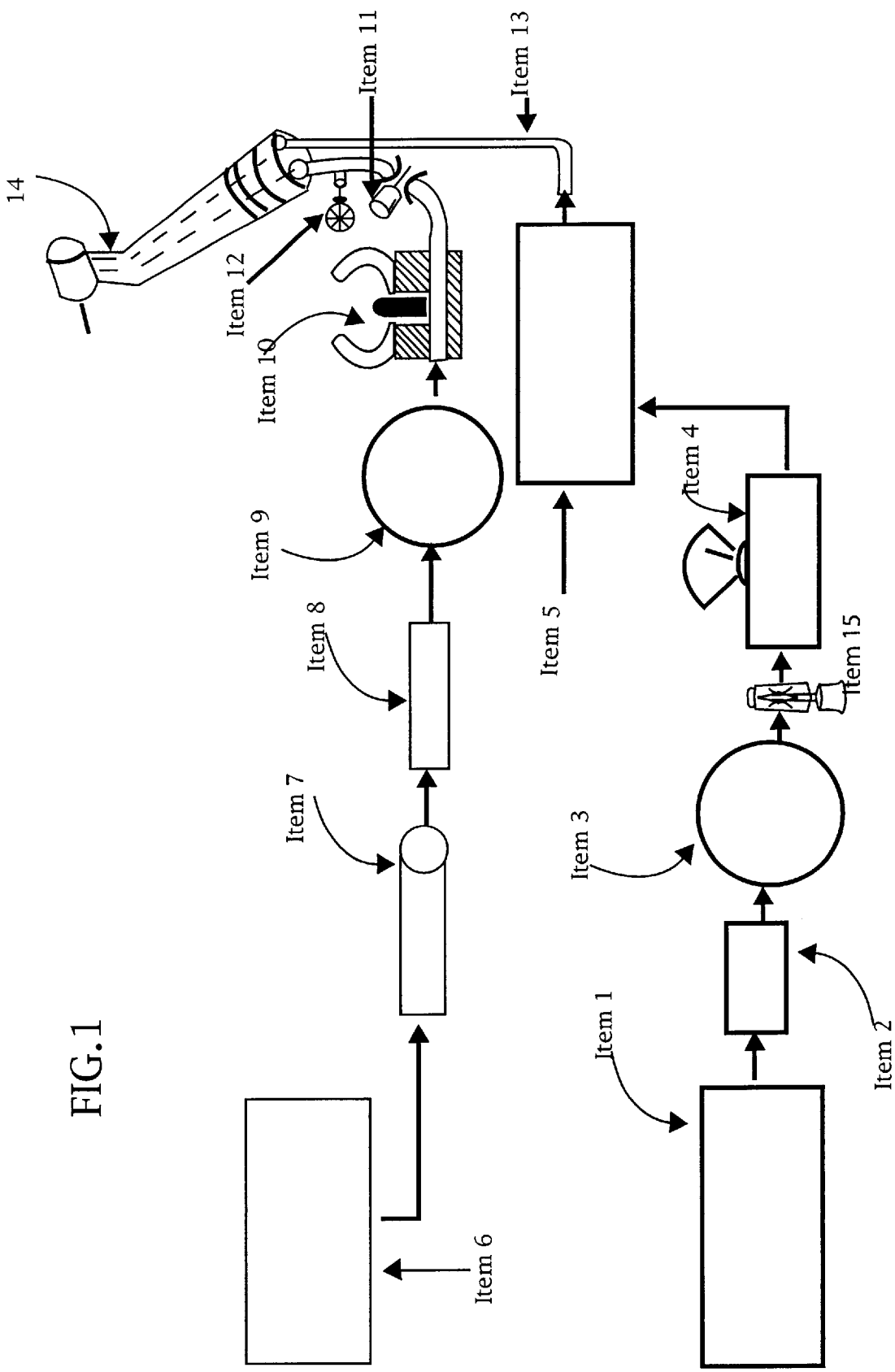
FIG. 1
Figure 1A:
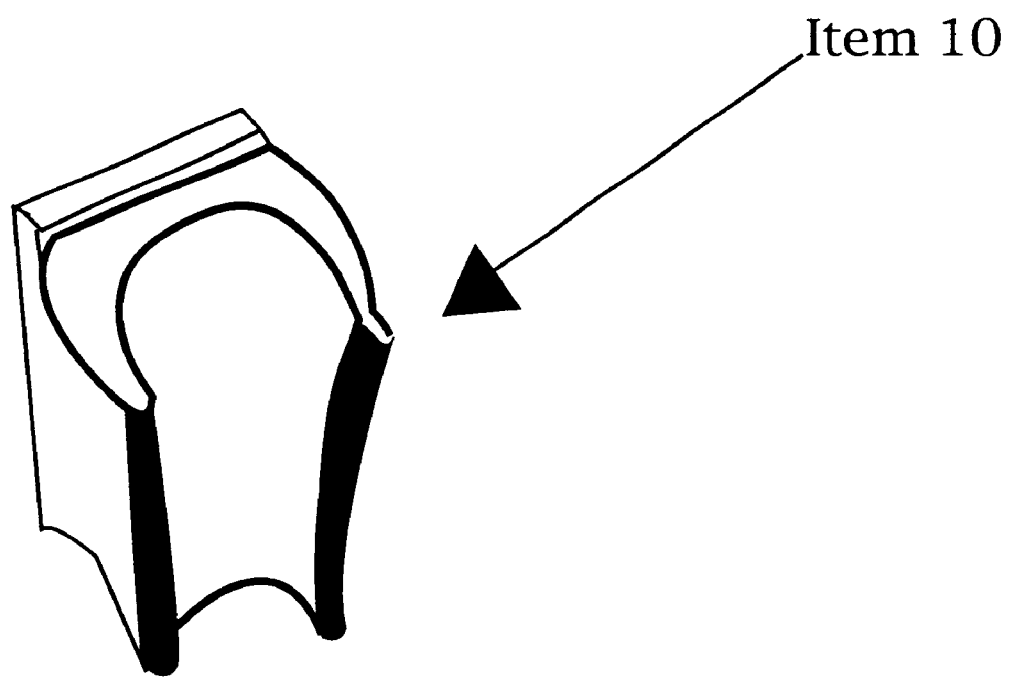

The Pressure Lever swinging on the fulcrum pin rides within the slot machined into the plastic holder FIG. 5a and the corresponding slot of the Back Plate, FIG. 6b, to facilitate the ON/OFF 'pinching' action on the flexible air tube FIG. 1, Item 13.

The function of the 'Pinch Valve' is unaltered.

DESCRIPTION OF THE PREFERRED EMBODIMENT

FIG. 1

This shows an overall circuit diagram of the Control System incorporating the essence of the present invention.

Item 10, the Pinch-Valve assembly, also the specific feature of the airflow path. This being an unseen element, patentable only by its' flow path pattern in relation to the actual circuit components in the order they are arranged (or positioned) to complete the circuitry.

FIG. 1 demonstrates a circuit drawing showing a One-Handpiece system. However, a multiple Handpiece Control system may also operate from a common Foot Control (Item 7) by merely 'linking up' two or more Pinch-Valve Assemblies in the air flow path. After the Main Regulator any number of tools or handpieces can be used. The one out of the holder being the only functioning Instrument. A source of compressed air (Item 6) and a source of water (Item 1) is typically available in all dental offices.

The source of compressed air (Item 6) is regulated by the Foot Control (Item 7) which provides variable airflow through the Filter (Item 8) to the Preset Air Regulator (Item 9). From this point it is 'fanned out' to one or more 'Pinch Valve' Assemblies (FIG. 1, Item 10). Following the airflow path as it leaves (FIG. 1, Item 10) it is pre-set by a Volume Control (FIG. 1, Item 11). The Air Pressure Gauge (Item 12) indicates that particular handpiece pressure reading (in p.s.i.) being used to specific air pressure requirements pertaining to the type of tool or handpiece recommendations specified by the manufacturers of the instruments.

DESCRIPTION OF A FURTHER EMBODIMENT

FIG. 1

This overall circuit diagram of the Control System remains unchanged, only the physical characteristics of the 'Pinch Valve' (FIG. 1) are altered. See drawings:

FIG. 5a The holder showing a slot, not a 'through' hole.

FIG. 5b The elongated, oval-shaped flat Disc (20), replacing the plunger.

FIG. 5c The Back Plate (16) with a change to a slot design to accept the Disc. The actual system functions are not affected.

This further embodiment allows the oval-shaped flat disc (20) (FIG. 5b) to 'pinch' the flexible air tube (FIG. 1, Item 13) into a flat state to create the OFF function when the tool or handpiece is replaced in position within the holder.

The actual function of the oval-shaped flat disc (20) (FIG. 5b) is achieved by being cradled inside the Back Plate (16) (FIG. 5c) as it rotates on the Fulcrum Pin, (FIG. 5b) by the action of the tool or handpiece touching the disc as it is removed and replaced by the operator. All other factors remain unchanged.

DESCRIPTION OF AN EVEN FURTHER EMBODIMENT

FIG. 5

This overall circuit diagram of the Control System remains unchanged, only the physical characteristics of the 'Pinch Valve' (FIG. 1, Item 10) are altered. See drawings:

FIG. 5a

The Holder—showing a slot, not a 'through' hole.

FIG. 6a

Figure 3:
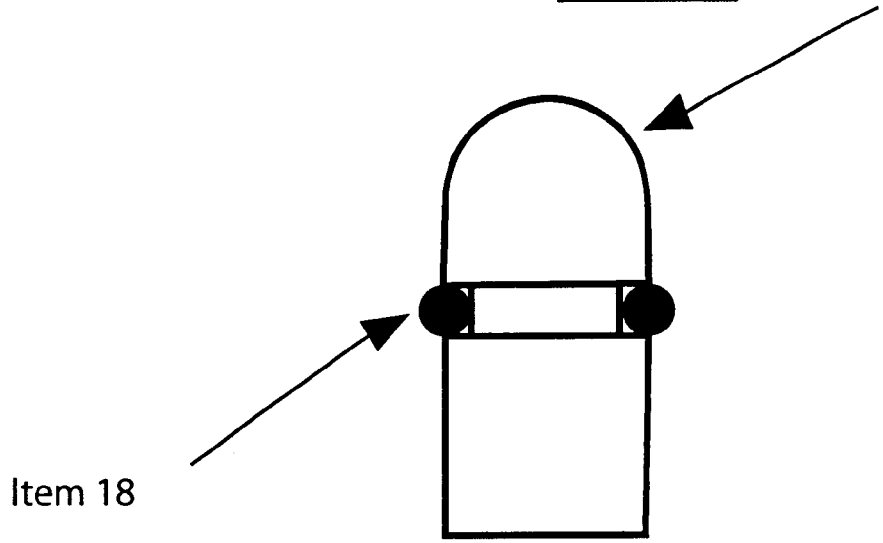

The Pressure Lever (21) replacing both the Plunger (17) and O-ring (18) as shown in FIG. 3 and the oval-shaped flat disc as shown in FIG. 5b.

FIG. 6b

The Back Plate (16) with the Fulcrum Pin (22) datum line raised to the top position of the Back Plate to allow the Lever swing movement.

The actual system functions are not affected.

This even further embodiment allows a Pressure Lever (21) (FIG. 6a) to 'Pinch' the flexible air tube (FIG. 1, Item 13) into a flat state to create the OFF function when the tool or handpiece is replaced in position with the holder.

The actual function of the Pressure Lever (21) is achieved by a pendulum type function as it moves backward and forward on the fulcrum pin (22) (FIG. 6a) by the action of the tool or handpiece touching the Pressure Lever as it is removed and replaced by the operator.

All other factors remain unchanged.

Operation of the 'Pinch Valve' Function as Described in the Preferred Embodiment With the tool or handpiece (FIG. 1, Item 14) at rest in the holder (FIG. No. 1, Item 10) the Plunger (17) (FIG. 3) is pressed DIRECTLY BACKWARDS and flattens the air flow tube (FIG. 1—1) Within The Handpiece Holder Assembly into the OFF state.

When the tool or handpiece (FIG. 1, Item 14) is removed from the holder (FIG. 1, Item 10) and the foot control (FIG. 1, Item 7) is depressed, the plunger (17) (FIG. 3) is forced outwards by the pressure of air passing through and inflating and expanding the flexible air flow tube (FIG. 1, Item 13) for the function of the ON state for instrument turbine performance.

This function of air only, spinning a handpiece turbine, without spray function, is termed: cutting dry. Should a spray function be required the circuit (FIG. 1) provides for water flow to the handpieces by selecting the Wet/Dry switch (FIG. 1, Item 4) to the ON position.

The volume of water flow which controls the spray function is pre-set by the operator (FIG. 1, Item 15) in relation to the clinical function being performed.

All instrument manufacturers establish air pressure limits, or specifications, that their tools or handpieces perform best at, for this purpose our circuitry (FIG. 1) incorporates a Volume Control Valve (FIG. 1, Item 11) for each handpiece being used.

An air pressure gauge (FIG. 1, Item 12) working in conjunction with the Volume Control Valve indicates the tool or handpiece pressure, in p.s.i., being used.

The operator turns the Control Knob clockwise to decrease pressure and anti-clockwise to increase pressure. When the required p.s.i. is established no further adjustment is needed.

When the operator completes the clinical and/or laboratory procedure the tool or handpiece is replaced in the holder.

This action of the tool or handpiece being pushed into the holder engages against the Plunger (17) (FIG. 3) forcing it back within the handpiece holder assembly (FIG. 1, Item 10) as described in the preferred embodiment; thereby 'pinching' flat a section of the flexible air flow tube (FIG. 1, Item 13) Within The Pinch Valve Holder Assembly and creating the OFF state, as explained in Paragraph 1, Sheet 14.

Figure 2:
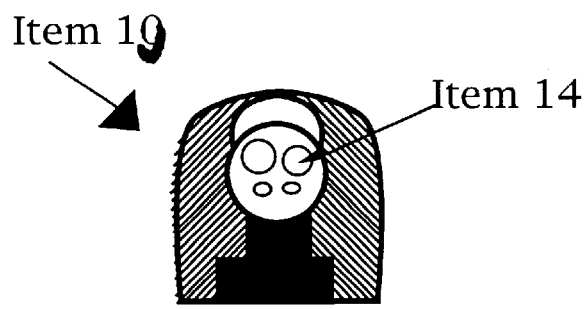
Figure 2A:
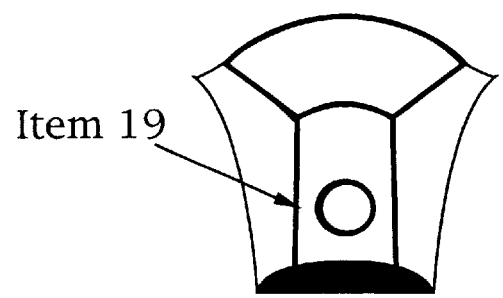
Figure 2A:
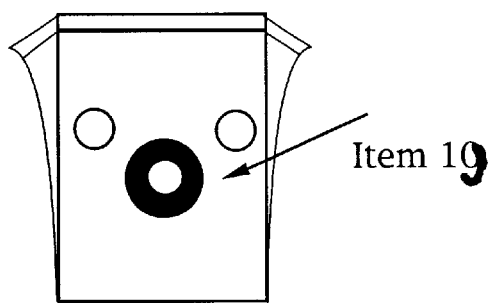
Figure 4:
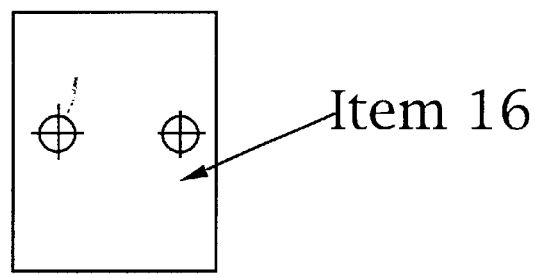
Figure 4A:
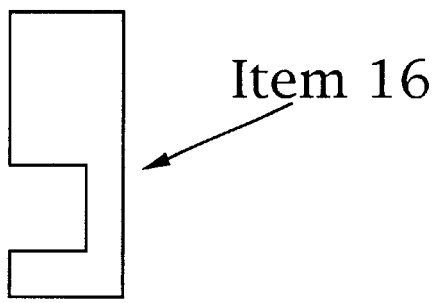
Figure 4B:
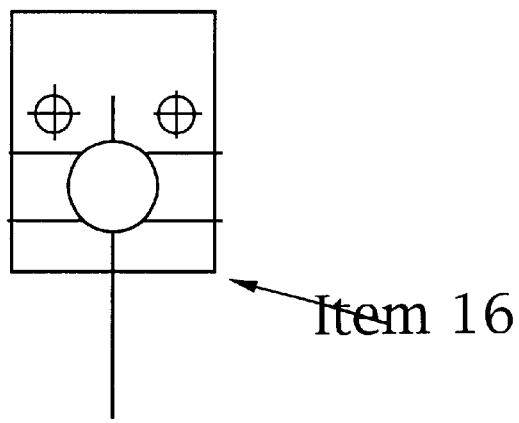

Operation of the 'Pinch Valve' Function as Described in the Further Embodiment A departure from the design of the 'Pinch Valve' Assembly as described in FIGS. 2, 2a and 2b; FIG. 3; FIGS. 4a and 4b changes the physical characteristics of these parts to a different configuration as described in FIGS. 5a, 5b, and 5c by the employment of an elongated oval-shaped flat disc

(20) (FIG. 5b) performing the same functions as demonstrated in the use of the 'Pinch Valve' as described in the preferred embodiment, action being:

Tool or handpiece replacement engages against the flat disc (20) (FIG. 5b) moving it backwards Within The Pinch Valve Holder Assembly (FIG. 1, Item 10) thereby creating the OFF state.

The ON state comes into effect when the tool or handpiece is removed from the holder and the foot control is depressed by the operator. This outward discharge of air passing through and inflating and expanding the flexible airflow tube (FIG. 1, Item 13) deploys the function of the 'Pinch Valve' Assembly into the ON state for instrument turbine performance.

Operation of the 'Pinch Valve' Function as Described in an Even Further Embodiment Another departure from the design of the 'Pinch Valve' assembly as described in FIGS. 2, 2a, and 2b; FIG. 3; FIGS. 4a and 4b covered under the preferred embodiment; also FIGS. 5a, 5b and 5c as depicted in the further embodiment design and function, emerges yet an even further embodiment classified as FIGS. 6a and 6b but utilizing the plastic holder modification (FIG. 5a) as an integral part of FIGS. 6a and 6b under the heading of 'Pinch Valve' Holder Assembly.

FIG. 6a being termed Pressure Lever (21) rotates backwards on the fulcrum pin (22) when the tool or handpiece or the handpiece hose coupling pushes against the Pressure Lever (21) and flattens the flexible air flow tubing (FIG. 1, Item 13) Within The 'Pinch Valve' Holder Assembly into the OFF state.

When the tool or handpiece is removed from the holder AND the Foot Control is depressed by the operator the outward flow of air being discharged inflates and expands the flexible air flow tube; FIG. 1, Item 13; thereby deploying the function of the 'Pinch Valve' assembly into the ON state for instrument turbine performance.

What I claim is:

1. A handpiece holder and control system, comprising a holder having a slot which is capable of storing a hand-held type handpiece, a pinch valve and a drive air tube which supplies drive air for operating the handpiece, the pinch valve located within the holder such that the pinch valve is directly engaged by a handpiece when held in the holder, the drive air tube extending through the holder and the pinch valve such that the pinch valve pinches the drive tube when a handpiece is located in the slot of the holder, and does not pinch the drive tube when a handpiece is removed from the holder.

2. The system of claim 1, wherein the pinch valve comprises a button type plunger.

3. The system of claim 1, wherein the pinch valve comprises a disc.

4. The system of claim 1, wherein the pinch valve comprises a lever and fulcrum pin.

5. The system of claim 1, further comprising a handpiece attached to the system.

* * * * *